United States Patent [19]

Allan et al.

[11] Patent Number: 4,554,155

[45] Date of Patent: Nov. 19, 1985

[54] CONTROLLED RELEASE COMPOSITIONS

[75] Inventors: George G. Allan, Seattle, Wash.; Amar N. Neogi, Greenville, N.C.

[73] Assignee: Washington Research Foundation, Seattle, Wash.

[21] Appl. No.: 640,428

[22] Filed: Dec. 15, 1975

Related U.S. Application Data

[63] Continuation of Ser. No. 434,083, Jan. 17, 1975, abandoned.

[51] Int. Cl.$^4$ .................... A01N 25/08; A01N 25/34
[52] U.S. Cl. ........................... 424/22; 424/19; 424/78; 71/DIG. 1; 514/777 CG
[58] Field of Search .................... 71/DIG. 1; 424/358–365

[56] References Cited

U.S. PATENT DOCUMENTS

| Re. 29,238 | 5/1977 | Dimitri et al. | 71/DIG. 1 |
| 2,714,553 | 8/1955 | Bibb et al. | 71/64 |
| 3,657,446 | 4/1972 | Blackmore | 424/274 |
| 3,705,467 | 12/1972 | McKnight | 47/9 |
| 3,737,551 | 6/1973 | Karsten et al. | 71/DIG. 1 |
| 3,813,236 | 5/1974 | Allan | 71/92 |
| 3,920,442 | 11/1975 | Albert et al. | 71/92 |
| 3,929,453 | 12/1975 | Dimitri et al. | 71/101 |
| 4,144,050 | 3/1979 | Frensch et al. | 71/DIG. 1 |
| 4,244,728 | 1/1981 | DelliColli et al. | 71/DIG. 1 |

FOREIGN PATENT DOCUMENTS

| 991694 | 10/1951 | France . |
| 991695 | 10/1951 | France . |
| 991696 | 10/1951 | France . |
| 991697 | 10/1951 | France . |
| 1164709 | 9/1969 | United Kingdom | 71/DIG. 1 |

OTHER PUBLICATIONS

Graham-Allan et al., Int. Pest. Contr: 15(1):4–7 (1973) Phytotoxicity of Some Systemic Insecticides to Spanish Cedar.
Pree et al., J. Econ. Entomol., 65(4):1081–1085, Aug. 1972, Chemical Control of the European Pine Shoot Moth.
Guilbaud et al., Chem. Abstr. 50, #9667D (1956) of Fr. Patents 991,694,-5-6-7.
G. G. Allan et al., Turrialba, 20(4): 478–487, Oct. Dec. 1970.
G. G. Allan et al., Int. Pest. Contr., pp. 4–11, Jul./Aug. 1974.
U.S.P.T.O. Translation of FR. 991694, Guilbaud et al.
U.S.P.T.O. Translation of FR. 991695, Guilbaud et al.
U.S.P.T.O. Translation of FR. 991696, Guibaud et al.
U.S.P.T.O. Translation of FR. 991697, Guilbaud et al.

Primary Examiner—Shep K. Rose
Attorney, Agent, or Firm—Seed and Berry

[57] ABSTRACT

Controlled release compositions releasing an effective amount of biologically active material such as pesticide into the environment over an extended period of time are disclosed. The compositions comprise an intimate admixture of an organic polymer and a component incorporating a biologically active material wherein the biologically active material is released by molecular diffusion through the matrix of the polymer at the surfaces exposed to the environment. The component including the biologically active material is incorporated in the polymer in amounts sufficient that diffusion of the component at the surfaces exposed to the environment results in loss of structural integrity and/or fraction of the polymer to thereby expose new surfaces to decomposition for further release of the biologically active material resulting in a rate of release over an extended period of time in proportion to that necessary to offer protection.

15 Claims, 2 Drawing Figures

CONTROLLED RELEASE COMPOSITIONS

This is a continuation of application Ser. No. 434,083 filed Jan. 17, 1975, now abandoned.

BACKGROUND OF THE INVENTION

1. Prior Art Relating to the Disclosure

A great deal of work has been carried out to increase the protection period of biologically active material such as pesticides which have relatively short lives while, at the same time, diminishing the residual waste of such pesticides which are the major cause of serious pollution problems and damage to wildlife. Systems have been developed which utilize the concept of "controlled release" to release the pesticide at a controlled rate effective to control the pest while minimizing the undesired contamination of water sources with subsequent damage to aquatic and wildlife. One method of accomplishing controlled release is by providing solid solutions of pesticides in polymers. U.S. Pat. No. 3,076,744 discloses a urea-formaldehyde resin incorporating up to 10 percent of an organic insecticide and an edible material attractive to insects. U.S. Pat. No. 3,269,900 discloses an intimate admixture of a polyurethane foam with a nonvolatile organic pesticide, the polyurethane foam forming a protective cover around the pesticide with release of the pesticide occurring gradually. U.S. Pat. No. 3,343,941 discloses physically admixing herbicidally active alkyd resins with other herbicides for slow release both by hydrolysis of the chemically incorporated herbicide as well as by physical release of the admixed herbicide. Canadian Pat. No. 846,785 discloses the incorporation of a pesticide in a thermoplastic polymer having desired permeability to the pesticide with release of the pesticide by diffusion of the pesticide through the polymer lattice.

The rate of release and length of protection afforded by the pesticide compositions disclosed in the above patents has not been commercially advantageous in many instances. The pesticide compositions disclosed in Canadian Pat. No. 846,785 release the pesticide rapidly at first and then too slowly to be effective for the purposes desired. Up to as much as 80 percent of the pesticide remains in the polymer after a reasonable period of time. Thereafter, the pesticide is released at too slow a rate to be effective. The rate of release of compositions disclosed in Canadian Pat. No. 846,785 is determined by the difference in pesticide concentration in the soil adjacent the polymer and that in the polymer surfaces exposed to the environment. Pesticide concentration sharply falls over a period of time, slowing the rate of release of the pesticide.

It has remained a problem to devise controlled release biologically active material compositions providing a release of a biologically active material over extended periods of time at effective rates for control. This application is directed to means providing release of the biologically active materials over an extended period of time and preventing the reduction of the release rate of the biologically active material from a biologically active material-polymer admixture below that necessary to be effective by continually exposing fresh surfaces of the polymer-biologically active material mixture to the environment.

SUMMARY OF THE INVENTION

The compositions described herein comprise an intimate mixture of an organic polymer and a component incorporating a biologically active mixture with or without a carrier material wherein the biologically active material is released to the environment by molecular diffusion through the lattice of the polymer at the surfaces exposed to the environment. A sufficient amount of the component is incorporated in the polymer so that diffusion of the component including the biologically active material at the surfaces exposed to the environment results in loss of structural integrity of the polymer and/or fracture thereof to thereby expose new surfaces of the biologically active material-polymer to the environment for further release of the component.

The objects of this invention are to provide controlled release compositions: (1) which have release rates effective for purposes desired over an extended period of time; (2) where loss of biologically active material in the composition at the surfaces of the composition exposed to the environment results in fracture and/or disintegration of the polymer at those surfaces to expose new surfaces to the environment for further diffusion of the biologically active material; (3) which in the case of pesticides, require much less pesticide for the same period of activity, are easier to handle, less toxic, provide lower risk of damage to plants, reduce toxicity to other organisms such as wildlife, reduce costs due to less frequent application and have minimal pollution hazard.

DETAILED DESCRIPTION OF THE INVENTION

Figure 1:
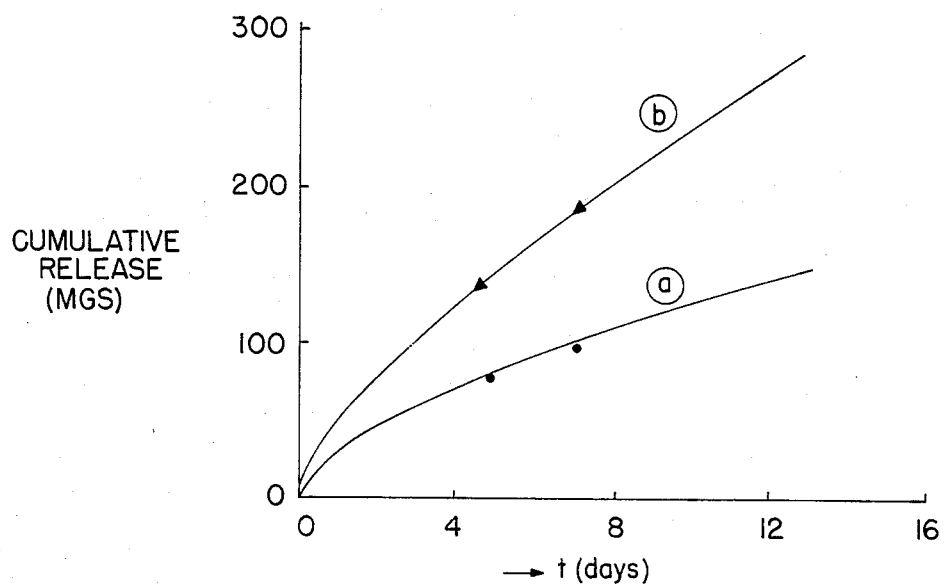
FIG. 1 is a graph of release rate vs. time of a composition made in accordance with this invention, and one prepared as described in Canadian Pat. No. 846,785.
Figure 2:
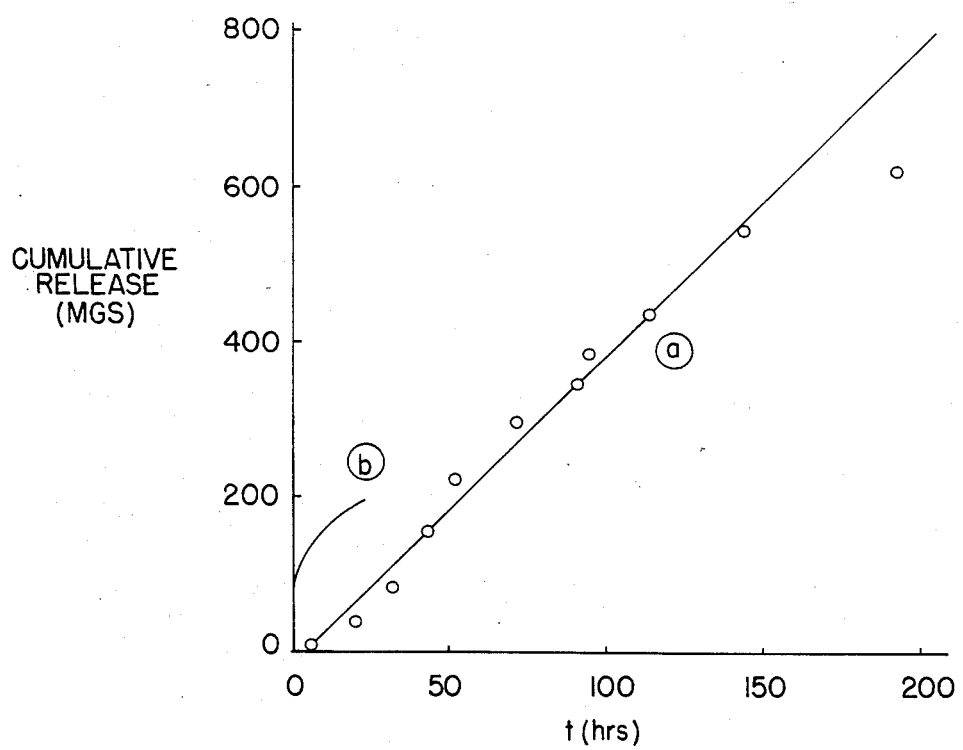
FIG. 2 is a graph of release rate vs. time for compositions, prepared as described in Canadian Pat. No. 846,785, compared with those of the present invention.

The following are definitions of terms as used herein in the specification:

Polymer—Natural or synthetic compounds having a multiple of their molecular weight which are water insoluble, inert with respect to the biologically active material incorporated therewith and permeable to the biologically active material incorporated therewith, i.e. the biologically active material is diffusible through the polymer lattice. The polymer may be a partial solvent for the biologically active material or the biologically active material a solvent for the polymer.

Biologically active material—Those compounds used to inhibit, repel, exterminate or alter the activities of insects, moles, fungi, bacteria, protozoa, viruses, plants, invertebrates, worms and the like and including medicinals, herbicides, insecticides, miticides, rodenticides, fungicides and the like which are non-reactive with the polymer used in conjunction therewith but soluble or dispersible therein; not thermally degraded at the temperatures used in formulating the admixture, and which may be water-soluble or insoluble.

Carrier—A material which enhances fracture of the composition by dissolution, degradation, etc. which may be monomeric or polymeric and which is compatible with the biologically active material and polymer used, inert with respect thereto, and preferably water soluble.

Pesticide Component—The pesticide alone or in admixture with a carrier.

Polymers used in preparation of the controlled release compositions of this invention may include: (1) synthetic polymers such as polyethylene, polypropylene, polystryrene, polyacrylates, polymethacrylates, polyamides, polyureas, ethylene-vinylacetate copolymers, ethylene-acrylic acid copolymers, polyvinylchloride, polyvinylidene chloride, polyesters, polyvinyl alcohols, cellulose acetate, cellulose triacetate, polyanhydrides, polyacetals, polyepoxides, polyethers, acrylonitrile-butadiene copolymers and styrenemaleic anhydride copolymers; (2) natural thermoplastic polymers such as natural gums and "Vinsol"-type resins (high melting, thermoplastic polymers derived from southern pine stump wood); (3) bitumens such as asphalt, asphaltites, asphaltic pyrobitumens and uintaite (Gilsonite); (4) rosins such as wood rosins, hydrogenated rosin, heat treated rosin, polymerized rosins and esterified rosins; and lignin or lignin derivatives. Preferred polymers include polyvinylacetate, Gilsonite and kraft lignin. The polymer should be of such type as to disintegrate after the active and/or inactive component leaves the composition.

Where the biologically active material is a pesticide selected for use in the controlled release compositions may be from those commercial pesticides now available including the following:

| | |
|---|---|
| N—sec-Butyl-4-tert-butyl-2,6-dinitroaniline | A-820 |
| 2-Chloro-4-ethylamino-6-isopropylamino-s-triazine | AAtrex |
| 0,0,0',0'-Tetramethyl 0,0'-thiodi-p-phenylene phosphorothioate | Abate |
| Isopropyl 4, 4'-dichloro benzilate | Acaralate |
| Isopropyl 4, 4'-dibromo-benzilate | Acarol |
| 2-Diethylamino-6-methyl-pyrimidin-4-yl dimethyl phosphorothionate | Actellic |
| 2-(0,0-Diethyl thionophosphoryl)-5-methyl-6-carbethoxypyrazolo-(1,5a) pyrimidine | Afugan |
| 2-[2-chloro-1-(2,5-dichloro-phenyl)-vinyl]0,0-diethyl phosphorothioate | Akton |
| n-Octanol 28% plus n-Decanol 38% | Alcohol C$_8$, C$_{10}$ |
| n-Decanol | Alcohol C$_{10}$ |
| 1, 2, 3, 4, 10, 10-Hexachloro-1, 4, 4a, 5, 8, 8a-hexahydro-1, 4 endo-exo-5, 8-dimethano-naphthalene | Aldrin |
| DL-2-Allyl-4-Hydroxy-3-methyl-2-cyclopenten-1-one esterified with a mixture of cis and trans DL-chrysanthemum monocarboxylic acid | Allethrin |
| 2-Propene-1-ol | Allyl alcohol |
| 3-Amino-2,5-dichlorobenzoic acid | Amiben |
| 3-Amino-1,2,4-triazole | Amitrole |
| 2-Propenal | Aqualin |
| 3-(4-Chlorophenyl)-1-methoxy-1-methylurea | Aresin |
| 4,6-Dinitro-2-sec-butylphenyl acetate | Aretit |
| 0,0,0,0-Tetrapropyl dithio-pyrophosphate | Aspon |
| Methy-4-aminobenzene sulfonyl-carbamate | Asulox |
| S—2,3-Dichloroallyl diisopropylthiocarbamate | Avadex |
| S—2,3,3-Trichloroallyl-diisopropyl thiocarbamate | Avadex BW |
| 2,6-di-tert-Butyl-p-tolylmethyl-carbamate | Azak |
| Dimethyl phosphate of 3-hydroxy-N—methyl-cis-crotonamide | Azodrin |
| Benzoyl chloride (2,4,6-trichlorophenyl) hydrazone | Banamite |
| 3,6-Dichloro-o-anisic acid | Banvel |
| 4-Chloro-2-butynyl-m-chloro-carbanitate | Barban |
| 2-Isopropoxyphenyl N—methyl-carbamate | Baygon |
| 2',5-Dichloro-4'-nitro-salicylanilide ethanolamine | Bayluscide |
| N—Butyl-N—ethyl-α,α,α-trifluoro-2,6-dinitro-p-toluidine | Benefin |
| Methyl-1-(butylcarbamoyl)-2 benzimidazole carbamate | Benomyl |
| Ethyl 0-benzoyl-3-chloro-2, 6-dimethoxybenzohydroximate | Benzomate |
| Methyl m-hydroxycarbanilate m-methylcarbanilate | Betanal |
| S—(0,0-Diisopropyl phosphorodithioate) ester of N—(2-mercaptoethyl)benzene-sulfonamide | Betasan |
| Dimethyl phosphate of 3-hydroxy-N,N—dimethyl-cis-crotonamide | Bidrin |
| 2-sec-Butyl-4,6-dinitrophenyl-3-methyl-2-butenoate | Binapacryl |
| 2-(4-Chloro-6-ethylamino-s-triazin -2-ylamino)-2-methyl-propionitrile | Bladex |
| S—(4-Chlorobenzyl)-N,N—diethylthiol carbamate | Bolero |
| Triphenyltinacetate | Brestan |
| 5-Bromo-3-sec-butyl-6-methyluracil | Bromacil |
| 3,5-Dibromo-4-hydroxybenzo-nitrile | Bromoxynil |
| 3,5-Dibromo-4-octanoyloxy-benzonitrile | Bromoxynil octanoate |
| m-(1-Methylbutyl)phenyl methyl-carbamate + m-(1-ethylpropyl)phenyl methylcarbamate | Bux Ten |
| Dimethyl arsinic acid | Cacodylic acid |
| 1-(p-tert-Butylphenoxy)-2-butyl 1-(2-butynyl)sulfite | Calamite |
| N—Tridecyl-2,6-dimethyl morpholine | Calixin |
| cis-N—((trichloromethyl)thio)-4-cyclohexene-1,2-dicarboximide | Captan |
| 1-Naphthyl methylcarbamate | Carbaryl |
| 2,3-Dihydro-2,2-dimethyl-7-benzofuranyl methylcarbamate | Carbofuran |
| m[[(Dimethylamino)methylene]-amino]phenyl methylcarbamate hydrochloride | Carzol |
| N—n-propyl-N—cyclopropylmethyl-4-trifluoromethyl-2,6-dinitroaniline | CGA-10832 |
| 0-(Methyl-2-propinylamino) phenyl N—methylcarbamate | CGA-13608 |
| Isopropyl N—phenylcarbamate | Chem Hoe |
| 3-(4-Bromo-3-chlorophenyl)-1-methoxy-1-methylurea | Chlorbromuron |
| Mixture of 60% octachloro-4,7-methanotetrahydroindane and 40% related compounds | Chlordane |
| N'—(4-Chloro-o-tolyl)-N,N—dimethylformamidine | Chlordimeform |
| Ethyl 4,4'-dichlorobenzilate | Chlorobenzilate |
| 1,4-Dichloro-2,5-dimethoxy benzene | Chloroneb |
| Trichloronitromethane | Chloropicrin |
| 3-[p-(p-chlorophenoxy)phenyl]- | Chloroxuron |

| | |
|---|---|
| 1,1-dimethylurea | |
| Isopropyl m,-chlorocarbanilate | Chlorpropham |
| Dimethyl phosphate of α-methylbenzyl 3-hydroxy-cis-crotonate | Ciodrin |
| N³,N³—Diethyl-2,4-dinitro-6-trifluoromethyl-m-phenylenediamine | Cobex |
| O,O-Diethyl O-3-chloro-4-methyl-2-oxo-2H—1-benzopyran-7-yl-phosphorothioate | Co-Ral |
| O-p-Cyanophenyl O,O-dimethyl phosphorothioate | Cyanox |
| 3-[2-(3,5-Dimethyl-2-oxocyclohexyl)-2-hydroxyethyl]-glutarimide | Cycloheximide |
| 2-(Diethoxyphosphinylimino)-1,3-dithiolane | Cyolane |
| Dodecylguanidine acetate | Cyprex |
| 2-(Diethoxyphosphinylimino) 4-methyl-1,3-dithiolane | Cytrolane |
| 2,4-Dichlorophenoxyacetic acid: also used as amine salts and esters | 2,4-D |
| 2,4,5,6-Tetrachloroisophthalonitrile | Daconil 2787 |
| Dimethyl-2,3,5,6-tetrachloroterephthalate | Dacthal |
| 2.2 Dichloropropionic acid | Dalapon |
| O,O-Diethyl O-[p-(methylsulfinyl)-phenyl]phosphorothioate | Dasanit |
| 4-(2,4-Dichlorophenoxy)butyric acid: also salt, amine salt and ester formulations | 2,4-DB |
| 1,2-Dibromo-3-chloropropane | DBCP |
| 2,6-Dichloro-4-nitroaniline | DCNA |
| 1,1,1-Trichloro-2,2-bis(p-chlorophenyl) ethane | DDT |
| S,S,S—Tributyl phosphorotrithioate | Def |
| O,O-Diethyl O-(2-isopropyl-6-methyl-4-pyrimidinyl)phosphorothioate | Diazinon |
| 2,6-Dichlorobenzonitrile | Dichlobenil |
| 2,3-Dichloro-1, 4-naphthoquinone | Dichlone |
| 2-(2,4-Dichlorophenoxy)-propionic acid | Dichlorprop |
| 2,2-Dichlorovinyl dimethyl phosphate | Dichlorvos |
| 1,1-bis(p-Chlorophenyl)-2,2,2-trichloroethanol | Dicofol |
| 1,2,3,4,10,10a, or a1,2,3,4,10, 10-hexachloro-6,7-epoxy-1,4,4a, 5,6,7,8,8a-octahydro-1,4-endo-exo-5,8-dimethanonaphthalene | Dieldrin |
| cis-N—[(1,1,2,2-Tetrachloroethyl)-thio]-4-cyclohexene-1,2-dicarboximide | Difolatan |
| O,O-Dimethyl S—(N—methylcarbamoyl-methyl) phosphorodithioate | Dimethoate |
| 2,4-Dimethylbenzyl 2,2-dimethyl-3-(2-methylpropenyl)cyclopropane-carboxylate | Dimethrin |
| 2-Dimethylcarbamyl-3-methyl-5-pyrazolyl dimethylcarbamate | Dimetilan |
| 2-(sec-Butyl)-4,6-dinitrophenol | Dinoseb |
| 2,3-p-Dioxanedithiol-S, S—bis (O,O-diethyl phosphorodithioate) | Dioxathion |
| 2-Methoxy-4H—1,3,2-benzodioxa-phosphorin-2-sulfide | Salithion |
| 2-Diphenylacetyl-1,3-indandione | Diphacin |
| N,N—Dimethyl-2,2-diphenyl-acetamide | Diphenamid |
| Diphenylamine | Diphenylamine |
| O,O-Diethyl-S—[2-(ethylthio)-ethyl]phosphorodithioate | Disulfoton |
| 3-(3,4-Dichlorophenyl)-1,1-dimethylurea | Diuron |
| 2-Methyl-4,6-dinitrophenol sodium salt | DNOC |
| DL-2-Allyl-4-hydroxy-3-methyl-2-cyclopenten-1-one esterified with D-trans chrysanthemum monocarboxylic acid | D-trans Allethrin |
| O,O-Diethyl O-(3,5,6-trichloro-2-pyridyl) phosphorothioate | Dursban |
| Triphenyltin hydroxide | Du-Ter |
| O-Ethyl-S—phenyl-ethylphos-phonodithioate | Dyfonate |
| O,O-Dimethyl (2,2,2-trichloro-1-hydroxyethyl)phosphonate | Dylox |
| 2,4-Dichloro-6-(o-chloroaniline)-s-triazine | Dyrene |
| 6,7,8,9,10,10-Hexachloro-1,5.5a, 6,9,9a-hexahydro-6,9-methano-2,4,3-benzodioxathiepin-3-oxide | Endosulfan |
| 7-Oxabicyclo(2.2.1)heptane-2,3-dicarboxylic acid | Endothall |
| 1,2,3,4,10,10-Hexachloro-6,7-epoxy-1,4,4a,5,6,7,8,8a-octahydro-1,4-endo-endo-5,8-dimethanonaphthalene | Endrin |
| Ethyl 3,7,11-trimethyl-dodeca-2,4-dienoate | Entocon ZR-512 |
| Isopropyl 11-methoxy-3,7,11-trimethyldodeca-2,4-dienoate | Entocon ZR-515 |
| O-Ethyl-O-p-nitrophenyl phenylphosphonothioate | EPN |
| S—Ethyl dipropylthiocarbamate | Eptam |
| 2-(2,4,5-Trichlorophenoxy) ethyl 2,2-dichloropropionate | Erbon |
| O,O,O',O'-Tetraethyl S,S'—methylene bisphosphorodithioate | Ethion |
| (2-Chloroethyl) phosphonic acid | Ethrel |
| 2-Ethyl-1,3-hexanediol | Ethyl hexanediol |
| 2-(Ethylamino)-4-(isopropylamino) = 6-(methylthio)-s-triazine | EVIK |
| 2,3,6-Trichlorophenylacetic acid or sodium salt | Fenac |
| O,O-Dimethyl-O-[4-(methylthio)-m-tolyl]-phosphorothioate | Fenthion |
| 1,1-Dimethyl-3-(α,α,α-trifluoro-m-tolyl)urea | Fluometuron |
| p-Nitrophenyl α,α,α,-trifluoro-2-nitro-p-tolyl ether | Fluorodifen |
| S,S,S—Tributyl phosphoro-trithioite | Folex |
| N—(Trichloromethylthio)-phthalimide | Folpet |
| Isomers of Benzenehexachloride containing 40% (by weight) of gamma isomer | Fortified Benzene Hexachloride |
| Contains 7.9% 2-(m-chlorophenoxy)-propionamide and 0.4% free acid- | Fruitone CPA |
| 3-(α-Acetonyl furfuryl)-4-hydroxycoumarin | Fumarin |
| 2-Chloro-1-(2,4,5-trichlorophenyl) vinyl dimethyl phosphate | Gardona |
| 2,4a,7-Trihydroxy-1-methyl-8-methylenegibb-3-ene-1,10-carboxylic acid-1 → 4 lactone | Gibberellic acid |
| Ethyleneglycol bis (trichloro-acetate) | Glytac |
| O,O-bis (p-Chlorophenyl) aceti-midoylphosphoramidothioate | Gophacide |
| O,O-Diethyl-s-[4-oxo-1,2,3-benzotriazin-3(4H)—ylmethyl]-phosphorodithioate | Guthion |
| 74% 1,4,5,6,7,8,8a-Heptachloro-3a,4,7a-tetrahydro-4,7-methano-indene | Heptachlor |
| 3-(Hexahydro-4,7-methanoinden-5-yl)-1,1-dimethylurea | Herban |
| Indole-3-butyric acid | Hormodin |
| 1-Phenyl-3-(O,O-diethylthio-nophosphoryl)-1,2,4-triazol | Hostathion |
| N—(Mercaptomethyl)phthalimide S—(O,O-dimethyl phosphoro-dithioate) | Imidan |
| Butyl 3,4-dihydro-2,2-dimethyl-4-oxo-1-2H—pyran-6-carboxylate | Indalone |
| 2,6-Dinitro-N,N—dipropyl-cumidine | Isopropalin |
| 2-(1-Methylheptyl)-4,6-dinitro-phenyl crotonate | Karathane |
| 3,5-Dichloro-N—(1,1-dimethyl-2-propynyl) benzamide | Kerb 50W |
| 3-Trifluoromethyl-4-nitrophenol, | Lamprecid |

| | |
|---|---|
| sodium salt | |
| Mixture of about 20% 2,3,5-Trimethylphenyl methylcarbamate; and 80% 3,4,5-trimethylphenyl-methylcarbamate | Landrin |
| 2-Chloro-2',6'-diethyl-N—(methoxymethyl)acetanilide | Lasso |
| 3-Cyclohexyl-6,7-dihydro-1H—cyclopentapyrimidine-2,4 (3H,5H)—dione | Lenacil |
| β-Butoxy-β'-thiocyanodiethyl ether | Lethane 384 |
| 1,2,3,4,5,6-Hexachlorocyclohexane containing at least 99% gamma isomer | Lindane |
| 3-(3,4-Dichlorophenyl)-1-methoxy-1-methylurea | Linuron |
| Phenyl 5,6-dichloro-2-trifluoro methylbenzimidazole-1-carboxylate | Lovozal |
| 2-Chloro-2',6'-diethyl-N—(butoxymethyl)-acetanilide | Machete |
| O,O-Dimethyl phosphorodithioate of diethyl mercaptosuccinate | Malathion |
| 1,2-Dihydro-3, 6-pyridazinedione | Maleic hydrazide |
| 4-(Dimethylamino)-m-tolyl methylcarbamate | Matacil |
| 2-Methyl-4-chlorophenoxyacetic acid | MCPA |
| 4-(2-Methyl-4-chlorophenoxy) butyric acid | MCPB |
| 2-(2-Methyl-4-chlorophenoxy) propionic acid | MCPP |
| S—(4,6-Diamino-s-triazin-2-yl-methyl) O,O-dimethyl | Menazon |
| 3,4-Dimethylphenyl-N—methyl carbamate | Meobal |
| 2-(4-Thiazolyl)benzimidazole | Mertect |
| 4-(Methylthio)-3, 5-xylylmethylcarbamate | Mesurol |
| 3-Methylphenyl-N—methyl carbamate | Metacrate |
| S—[2-(Ethylsulfinyl)ethyl] O,O-dimethyl phosphorothioate | Meta-Systox R |
| S—Methyl N—[(methylcarbamoyl)-oxy]thioacetimidate | Methomyl |
| 2,2-bis (p-Methoxyphenyl)-1,1,1-trichloroethane | Methoxychlor |
| Methyl nonyl ketone | Methyl nonyl ketone |
| O,O-Dimethyl O-p-nitrophenyl phosphorothioate | Methyl parathion |
| 3-(p-Bromophenyl)-1-methoxy-1-methylurea | Metrobromuron |
| 2-Carbomethoxy-1-methylvinyl dimethyl phosphate, α isomer | Mevinphos |
| N—(2-Ethylhexyl) bicyclo[2.2.1]-5-heptene-2, 3-dicarboximide | MGK 264 |
| 2,3,4,5-bis (2-Butenylene)tetrahydrofurfural | MGK Repellent 11 |
| Dipropyl isochinchomeronate | MGK Repellent 326 |
| 2-Hydroxyethyl-n-octyl sulfide | MGK Repellent 874 |
| Scilliroside glycoside | MGK Rodenticide |
| 5-Butyl-2-dimethylamino-4-hydroxy-6-methylpyrimidine | Milcurb |
| 5-Butyl-2-ethylamino-4-hydroxy-6-methylpyrimidine | Milstem |
| Dodecachlorooctahydro-1,3,4-metheno-1H—cyclobuta[cd]-pentalene | Mirex |
| 4-Benzothienyl-N—methylcarbamate | Mobam |
| O-Ethyl S, S—dipropyl phosphorodithioate | Mocap |
| O,S—Dimethyl phosphoroamidothioate | Monitor |
| 3-(p-Chlorophenyl)-1,1-dimethylurea | Monuron |
| 3-(4-Chlorophenyl)-1, 1-dimethylurea trichloroacetate | Monuron TCA |
| 6-Methyl-2,3-quinoxalinedithiol cyclic-S, S—dithiocarbonate | Morestan |
| 1,2-Dibromo-2,2-dichloroethyl dimethyl phosphate | Naled |
| 1-Naphthalene acetamide | Naphthalene acetamide |
| 1-Naphthaleneacetic acid | Naphthalene acetic acid |
| 1-n-Butyl-3(3,4-dichlorophenyl)-1-methylurea | Neburon |
| O—Phenyl,N,N'-dimethylphosphoro-diamidate | Nellite |
| Ethyl 4-(methylthio)-m-tolyl isopropylphosphoramidate | Nemacur |
| 2,2-Dimethyl-3-(2-methylpropenyl) cyclopropanecarboxylic acid ester of N—(hydroxymethyl)-1-cyclohexane-1,2-dicarboximide | Neo-Pynamin |
| Ethyl hydrogen 1-propyl phosphonate | Nia 10637 |
| 1-Propylphosphonic acid | Nia 10656 |
| 6-tert-Butyl-3-isopropylisothia-zolo-(3,4-d)pyrimidin-4(5H)—one | Nia 19873 |
| 6-tert-Butyl-3-isopropylisoxazo-lo-(5,4-d)pyrimidin-4(5H)—one | Nia 21844 |
| 6-tert-Butyl-3-propylisoxazolo-(5,4-d)pyrimidin-4(5H)—one | Nia 21861 |
| 6-tert-Butyl-3-isopropylisoxazolo-(3,4-d)pyrimidin-4(5H)—one | Nia 23486 |
| 3-(1-Methyl-2-pyrrolidyl)pyridine | Nicotine |
| 2,4-Dichlorophenyl p-Nitrophenyl ether | Nitrofen |
| 2,-Chloro-6-(trichloromethyl) pyridine | N-Serve |
| N—(3,5-Dichlorophenyl)succinide | Ohric |
| 2-(p-tert-Butylphenoxy) cyclohexyl 2-propynyl sulfite | Omite |
| S—Ethyl hexahydro-1H—azepine-1-carbothioate | Ordram |
| O,S—Dimethyl acetylphosphoramidothioate | Orthene |
| 2-sec Butyl phenyl-N—methyl carbamate | Osbac |
| 2-Chloro-4-(cyclopropylamino)-6-(isopropylamino)-s-triazine | Outfox |
| O,O-Diethyl O-p-nitrophenyl phosphorothioate | Parathion |
| α,α-bis(p-Chlorophenyl)-3-pyridine methanol | Parinol |
| Pentachloronitrobenzene | PCNB |
| Pentachlorophenol | PCP |
| Decachlorobis(2,4-cyclopentadiene-1-yl) | Pentac |
| 1,1-Dichloro-2,2-bis(p-ethylphenyl) ethane (88%) plus related compounds, 12% | Perthane |
| Dibenzo 1,4-thiazine | Phenothiazine |
| O,O-Dimethyl S—(α-ethoxycarbonylbenzyl)-phosphorodithioate | Phenthoate |
| O,O-Diethyl S—(ethylthio)-methyl phosphorodithioate | Phorate |
| Tributyl 2,4-dichlorobenzylphosphonium chloride | Phosfon |
| 2-Chloro-N,N—diethyl-3-(dimethoxyphosphinyloxy)crotonamide | Phosphamidon |
| O-(4-Bromo-2,5-dichlorophenyl) O-methyl phenylphosphonothioate | Phosvel |
| 4-Amino-3,5,6-trichloropicolinic acid | Picloram |
| 3-(2-Methylpiperidino)propyl 3,4-dichlorobenzoate | Piperalin |
| 2-Dimethylamino-5, 6-dimethylpyrimidin-4-yl dimethylcarbamate | Pirimor |
| 4-(Methylsulfonyl)-2, 6-dinitro-N,N—dipropylaniline | Planavin |
| 5,6-Dihydro-2-methyl-1,4-oxathiin-3-carboxanilide,4,4-dioxide | Plantvax |
| Tricyclohexyltin hydroxide | Plictran |
| 2-Diethylamino-6-methylpyrimidin-4-yl diethyl phosphorothioate | Primicid |
| 2-Chloro-4,6-bis (ethylamino)-s-triazine | Princep |
| 2-(3,4-Dichlorophenyl)-4-methyl-1,2,4-oxadiazolidine-3,5-dione | Probe |
| 2,4-bis(Isopropylamino)-6-methoxy-s-triazine | Prometone |
| 2,4-bis(Isopropylamino)-6-(methylthio)-s-triazine | Prometryne |
| 3,4-Dichloropropionanilide | Propanil |
| 2-Chloro-4,6-bis(isopropylamino)-s-triazine | Propazine |
| Di-n-propyl 6,7-methylenedioxy-3-methyl-1,2,3,4-tetrahydrona- | Propyl isome |

| -continued | |
|---|---|
| phthalene-1,2-dicarboxylate | |
| 1,8-Naphthalic anhydride | Protect |
| 5-Amino-4-chloro-2-phenyl-3(2H)—pyridazinone | Pyramin |
| 2-Chloro-N—isopropylacetanilide | Ramrod |
| N,N—Diallyl-2-chloroacetamide | Randox |
| (5-Benzyl-3-furyl)methyl-2,2-dimethyl-3-(2-methyl-propenyl)cyclopropanecarboxylate | Resmethrin |
| S—Ethyl N—ethyl-N—cyclohexylthiocarbamate | Ro-Neet |
| 0,0-Dimethyl-0-(2,4,5-trichlorophenyl) phosphorothioate | Ronnel |
| 2-tert-Butyl-4-(2,4-dichloro-5-isopropyloxyphenyl)-5-oxo-1,3,4-oxadiazoline | Ronstar |
| Rotenone | Rotenone |
| 2,5 Dimethyl-1-pyrrolidinecarboxanilide | Rowtate |
| 4-tert-Butyl-2-chlorophenyl 0-methyl methylphosphoroamidate | Ruelene |
| Succinic acid 2,2-dimethylhydrazide | SADH |
| 2-Methoxy-4H—1,3,2-benzodioxaphosphorin-2-sulfide | Salithion |
| 2-Ethylthio-4,6-bis-isopropylamino-s-triazine | Sancap |
| 4-Amino-6-t-butyl-3-(methylthio)-1,2,4-triazin-5(4H)—one | Sencor |
| 2-Methyl-5,6-dihydro-4-H—pyran-3-carboxylic acid anilide | Sicarol |
| 1-(2-Methylcyclohexyl)-3-phenylurea | Siduron |
| 2-(2,4,5-Trichlorophenoxy)-propionic acid | Silvex |
| 6-Ethoxy-1,2-dihydro-2,2,4-trimethylquinoline | Stop Scald |
| 2,4-Diguanidino-3,5,6-trihydroxycyclohexyl 5-deoxy-2-0-(2-deoxy-2-methyl-amino-α-glucophyranosyl)-3-formyl pentanofuranoside | Streptomycin |
| 1-Methyl-2-(3,4-methylenedioxyphenyl) ethyl octyl sulfoxide | Sulfoxide |
| 0,0-Dimethyl 0-(4-nitro-m-tolyl)-phosphorothioate | Sumithion |
| 2-sec-Butylamino-4-ethylamino-6-methoxy-s-triazine | Sumitol |
| 0,0-Dimethyl S—(2-methoxy-1,3,4-thiadiazol-5(4H) onyl-4-methyl phosphorodithioate | Supracide |
| 0-p-Cyanophenyl 0-ethylphenyl-phosphonothioate | Surecide |
| S-13 Ethyl diisobutylthiocarbamate | Sutan |
| A 2:1 mixture of 0,0-diethyl-0-[2-(ethylthio)ethyl]phosphorothioate (thiono isomer) I and 0,0-diethyl-S—[2-(ethylthio)ethyl] phosphorothioate (thiolisomer) II | Systox |
| 2,4,5-Trichlorophenoxyacetic acid | 2,4,5-T |
| m-(3,3-Dimethylureido)phenyl tert-butylcarbamate | Tandex |
| Dimethylamine salt of 2,3,6-trichlorobenzoic acid and other trichlorinated benzoic acids | 2,3,6-TBA |
| Trichloroacetic acid, sodium salt | TCA |
| Trichlorobenzylchloride | TCBC |
| Tetrachlorothiophene | TCTP |
| 2-Methyl-2-(methylthio)propionaldehyde 0-(methylcarbamoyl)-oxime | Temik |
| Tetraethyl purophosphate | TEPP |
| 3-tert-Butyl-5-chloro-6-methyl-uracil | Terbacil |
| 2-tert-Butylamino-4-ethylamino-6-methylthio-s-triazine | Terbutryn |
| 5-Ethoxy-3-trichloromethyl-1,2,4-thiadiazole | Terrazole |
| 4'-Chlorophenyl2,4,5-trichlorophenyl sulfone | Tetradifon |
| Isobornyl thiocycanoacetate (82%) and related compounds | Thanite |
| Diethyl 4,4'-o-phenylene-bis (3-thioallophanate) | Thiophanate E |
| Dimethyl 4,4'-o-phenylene-bis (3-thioallophanate) | Thiophanate M |
| bis(Dimethylthiocarbamoyl)disulfide | Thiram |
| 1,4-Dithiaanthraquinone-2,3-di-carbonitrile | Thynon |
| 2,3,5-Triiodobenzoic acid | Tiba |
| S—Propyl butylethylthiocarbamate | Tillam |
| S—(2-Chloro-1-phthalimido-ethyl)-0 0-diethyl phosohorodithioate | Torak |
| N,N—bis(2-chloroethyl)-2,6-dinitro-p-toluidine | Torpedo |
| Chlorinated camphene with 67-69% chlorine | Toxaphene |
| α,α,α-Trifluoro-2,6-dinitro-N,N—dipropyl-p-toluidine | Trifluralin |
| S—[[(p-Chlorophenyl)thio]methyl] 0,0-diethyl phosphorodithioate | Trithion |
| Piperonal bis [2-(2'-n-butoxy-ethoxy)ethyl]acetal | Tropital |
| 3-Phenyl-1, 1-dimethylurea trichloroacetate | Urab |
| 0-2, 4-Dichlorophenyl 0, 0-diethyl phosphorothioate | VC-13 |
| 2-Chloroallyl diethyldithio-carbamate | Vegadex |
| S—Propyl dipropylthiocarbamate | Vernam |
| 5,6-Dihydro-2-methyl-1,4-oxathiin-3-carboxanilide | Vitavax |
| 4-Dimethylamino 3,5-xylyl methylcarbamate | Zectran |
| 0,0-Diethyl-2-(2-pyrazinyl) phosphorothioate | Zinophos |
| 0,0-Diethyl S[(6-chloro-2-oxo-benzoxazolin-3-yl)methyl] phosphorodithioate | Zolone |

Preferred are pesticides which act through the root system of the plant, such as organophosphorus, carbamate and phenoxyacid pesticides and particularly the following pesticides: 2,4-dichlorophenoxyacetic acid (2,4-D) and 2,3-dihydro-2,2-dimethyl-7-benzofuranyl methylcarbamate (Carbofuran).

The polymer and pesticide or pesticide and carrier are physically admixed generally by heating the solid polymer to the liquid state and then thoroughly admixing, at that temperature, the desired pesticide or pesticide and carrier until a uniform distribution is obtained.

The choice of a particular polymer with a particular pesticide is determined by a number of factors. One of the most important is the ability of the pesticide to diffuse through the polymer lattice. In general, the pesticide and polymer must be mutually compatible. The amount of pesticide or pesticide and carrier incorporated in the polymer, in the case of a substantially non-biodegradable polymer must be sufficient to induce stresses within the structure of the composition of diffusion of the pesticide from the polymer at those surfaces exposed to the environment so that the polymer-pesticide or polymer-pesticide-carrier combination will lose its structural integrity at those surfaces exposed to the environment to expose fresh surfaces to the soil environment. If the pesticide component is used alone, it must generally be incorporated within the polymer in amounts greater than 50 percent by weight so that the pesticide forms the matrix of the composition although lower percentages can be used with kraft lignin because of the low cohesivity of this polymer. As the pesticide diffuses into the environment at the exposed surfaces of the composition, the polymer left behind loses its structural integrity and fractures or disintegrates exposing new surfaces of the composition to the environment for further diffusion thereof. When the pesticide is admixed with a carrier and incorporated into the polymer, the amount of pesticide-carrier should usually be greater than 50 percent by weight.

The carrier may be a water-soluble monomeric or polymeric material which is compatible with the polymer and the pesticide, nontoxic for the desired use and diffusable through the polymer lattice. The carrier may also be a polymeric material which is biodegradable in the environment in which the composition is to be used, such as cellulosic fibers, urea-formaldehyde polymers, etc. Examples of water soluble carriers which may be used include polyethylene glycols having molecular weights ranging from 600 to 6000, biodegradable monomeric materials such as maleic anhydride, tartaric acid, etc.

In the case of a biodegradable polymer such as kraft lignin the amount of pesticide or pesticide-carrier incorporated in the polymer should be at least the amount, when released, to effectively control the pest. The amount may range from 15 wt. % to 50 wt. % or greater. The biodegradable polymer-pesticide composition peels away at the soil-composition interface after release of the pesticide incorporated therewith to expose new surfaces of polymer-pesticide to the environment.

The relative amounts of carrier and pesticide used in the controlled release composition may range from 0 to 80 percent carrier to 100 to 20 percent pesticide.

The controlled release compositions may be and are generally cast in pellet form of any desired shape for ease of use and transportation. The pellets, when incorporating a pesticide, are either incorporated in the soil around the area desired to be treated or spread on the surface of the soil with release of the pesticide occurring over an extended period of time by diffusion from the composition into the soil environment surrounding the pellets.

The following examples are illustrative of the invention but are not intended to be limiting in any manner.

EXAMPLE 1

Pesticide-polymer prepared according to Canadian Pat. No. 846,785.

One part of 2,4-dichlorophenoxyacetic acid was blended with one part of molten polyvinyl acetate and cast into a block having a surface area of 20 square centimeters. The block was immersed in 500 ml. of water and the release rate of the pesticide into the water determined over a period of time. The results illustrated by FIG. 1 (Curve A) clearly show that the rate of release of the pesticide is initially rapid and then diminishes with time.

EXAMPLE 2

A mixture of one part 2,4-dichlorophenoxyacetic acid was admixed with one part of a 1:1 mixture of molten polyvinyl acetate and a water soluble polyoxyethylene glycol polymer having a molecular weight of about 6000. The molten composition was cast into a block having a surface area of 20 square centimeters and immersed in 500 ml. of water. The release rate of the pesticide was measured at various time intervals. Curve B in FIG. 1 clearly shows that the amount of pesticide released does not diminish with passage of time but is substantially constant.

EXAMPLE 3

Molten Gilsonite was mixed with varying amounts of Carbofuran to prepare pesticide-polymer compositions containing 10%, 20%, 30% and 50% by wt., respectively, of Carbofuran. Each of the homogeneous compositions was cast into plate form. The release rate of each of the compositions was determined by dipping the plates of the respective compositions in water (25 ml.) and withdrawing the plates from the water at varying time intervals for analysis by total UV determination. The release rates of the compositions containing 10% to 40% by wt. of Carbofuran were insignificant while the compositions containing 50% by wt. of Carbofuran showed significant release rates. The release rates of the 50% by wt. Carbofuran composition remained substantially constant over an extended period of time.

EXAMPLE 4

Kraft lignin (10 gm.) was dissolved in dry dioxane (500 ml.) after which dioxane (350 ml.) was evaporated off. Carbofuran (5 gm.) in dioxane (50 ml.) was then added and most of the solvent removed under reduced pressure. The viscous mixture was poured into a Waring blender containing hexane (500 ml.). The mixture was filtered, air-dried and pelletized. The pellets contained about 25 wt. percent of Carbofuran.

EXAMPLE 5

Kraft-lignin-Carbofuran mixtures were prepared similar to that of Example 4 with varying concentrations of Carbofuran. The mixtures were pressed into wafers or cast into cylinders and used in field tests by placing them in the soil around young trees (*Sweitenia macrophylla*) in Costa Rica. A randomized block approach was employed with 15 blocks of 16 trees each for a total of 240 trees. Within each block of trees was one replicate each of three formulations in three levels each. In seven blocks three additional formulations in one level each were included. The formulations and treatment levels were as follows:

| Formulation | Treatment Level (per tree) | Designation |
|---|---|---|
| A. Kraft-lignin-Carbofuran wafers | 2 pellets | L1 |
| 59.3% Carbofuran | 3 pellets | L2 |
| 9.8 cm$^2$/pellet (avg. area) | 4 pellets | L3 |
| 1.28 g/pellet | | |
| B. Kraft-lignin-Carbofuran cylinders | 3 pellets | C1 |
| 57.6 Carbofuran | 4 pellets | C2 |
| 4.35 cm$^2$/pellet (avg. area) | 6 pellets | C3 |
| 0.73 g/pellet | | |
| C. Kraft-lignin-Carbofuran cylinders | | |
| 79.9% Carbofuran | | |
| 4.86cm$^2$/pellet (avg. area) | 4 pellets | C4 |
| 0.439 g/pellet | | |
| D. Kraft-lignin-Carbofuran cylinders | | |
| 89.2% Carbofuran | | |
| 2.92 cm$^2$/pellet (avg. area) | 4 pellets | C5 |
| 0.42 g/pellet | | |

A block of trees was selected at random after each two week period, infested with 20 eggs/tree of the *Hypsipyla grandella* shootborer pest and observed for survival of larvae and damage. Additionally, samples of fresh leaves from the trees were selected and bioassayed in the laboratory with first instar Hypsipyla larvae. To be considered "toxic", as indicated in Table I, a tree had to both withstand the field infestation with an intact terminal and complete larvae mortality and also kill the larvae in the laboratory bioassay. Trees which exhibited poor growth or died were eliminated from the results. As Table I indicates, about 27% of the trees on the alloted site were eliminated due to the poor conditions of the site. The blocks were only able to be monitored for six months in the manner set out before drought conditions set in and prematurely aborted the experiment.

In Table I those marked with zeros are those tree eliminated from the results due to poor growth or death. The "control" (an average of 60 untreated trees) had a "percentage effectiveness" of 11.9% compared with the most successful test (C3) of 80%. Tests L1, L2 and L3, releasing, on the average, about 40% of the available Carbofuran in six months were not too effective in controlling the pest, probably because of inadequate-active released Carbofuran to cover the root system of the trees.

Tests C1 to C3 released, on the average, about 50% of their available Carbofuran in six months. Test C3 (6 pellets/tree) was about 80% effective in controlling the pest.

Tests C4 and C5, employing more concentrated mixtures of Carbofuran released, on the average, about 49% of the available Carbofuran in six months. The low percentage effectiveness was apparently due to inadequate active Carbofuran in the soil over an area sufficient to cover the root system of the tree.

material, escapes from the composition, resulting in loss of the structural integrity and disintegration of the outer surfaces only of the composition to expose new, undisintegrated surfaces of the composition containing the diffusible component for further release thereof.

2. The composition of claim 1 wherein the solid solution is formed by heating the biologically active pesticide material to the liquid state and thoroughly admixing the polymer and diffusible component with the biologically active pesticide material in the liquid state until the polymer and component are uniformly distributed throughout the biologically active pesticide material.

3. The composition of claim 1 wherein the diffusible component is present in the composition in an amount equal to or greater than 50 percent by weight relative to the water-insoluble biodegradable organic polymer so that the diffusible component forms the matrix of the composition and wherein the diffusible component contains a major amount of the biologically active pesticide material.

4. The solid, control release, biologically active pesticide material delivery composition of claim 1 wherein the diffusible component includes a major amount of a biologically active pesticide material and a minor amount of a water-soluble substance inert with respect to the biologically active pesticide material, the diffusible component present in an amount equal to or greater

TABLE I

| Elapsed Time (days) | 30 | 43 | 61 | 76 | 91 | 107 | 125 | 138 | 153 | 169 | 183 | Amount of Active Ingredient | | Percentage Effectiveness |
|---|---|---|---|---|---|---|---|---|---|---|---|---|---|---|
| Block No. | 8 | 14 | 5 | 12 | 3 | 4 | 2 | 10 | 6 | 13 | 9 | Applied (g) | Released in 6 months | |
| Treatments | | | | | | | | | | | | | | |
| L1 | + | + | + | − | + | − | + | − | − | − | + | 1.3 | 0.56 | 54% |
| L2 | − | − | 0 | + | − | + | + | − | − | − | − | 2.2 | 0.85 | 30 |
| L3 | − | − | + | − | − | − | − | − | − | + | + | 3.1 | 1.13 | 27 |
| C1 | − | 0 | − | − | − | − | − | − | − | − | − | 1.2 | 0.63 | 0 |
| C2 | + | 0 | − | 0 | + | − | − | − | − | − | + | 1.7 | 0.84 | 33 |
| C3 | + | + | + | + | − | − | + | 0 | + | + | + | 2.7 | 1.26 | 80 |
| C4 | 0 | 0 | − | 0· | + | − | 0 | − | − | 0 | 0 | 1.7 | 0.88 | 20 |
| C5 | 0 | 0 | − | 0 | − | − | 0 | − | − | 0 | 0 | 1.5 | 0.72 | 0 |
| Control* | | | | | | | | | | | | 0.0 | 0.0 | 11.9 |

*Average of 60 trees.
+ = toxic
− = not toxic
0 = not treated, tree dead or unhealthy The embodiments of the invention in which a particular property or privilege is claimed are defined as follows:

1. A solid, controlled release, biologically active pesticide material delivery composition for release of the biologically active pesticide material over an extended period of time into the surrounding environment by molecular diffusion of the biologically active pesticide material through the matrix of the composition from the surfaces of the composition exposed to the environment, the composition consisting essentially of:
  a solid solution of kraft lignin and a biodegradable water-insoluble organic polymer which is soluble in the biologically active pesticide material in a diffusible component which includes a biologically active pesticide material non-reactive with the organic polymer, the diffusible component present at least a 15 wt.% concentration in the composition that when the outer surfaces of the composition are exposed to the environment, the diffusible component, including the biologically active pesticide than 50 percent by weight relative to the organic polymer and wherein the water-soluble substance diffuses simultaneously with the biologically active pesticide material.

5. A method of protecting plants from pests over an extended period of time, comprising:
  applying to the environment in which the plant to be protected is located an amount of a pesticide composition effective to control the pest, the composition consisting essentially of kraft lignin as a biodegradable solid solution of a water-insoluble, solid organic polymer which is soluble in the pesticide in a diffusible component, including a pesticide which is non-reactive with the organic polymer, the diffusible component present in the composition at least at 15 wt.% a concentration that when the outer surfaces of the composition are exposed to the environment, the diffusible component, including the pesticide, escapes from the composition, resulting in loss of the structural integrity and disintegration of the outer surfaces only of the composition to expose new, undisintegrated surfaces of the composition containing the diffusible component for further release thereof over an extended period of time until the component and the organic polymer are substantially dissipated.

6. A solid, controlled release pesticide composition from which the pesticide is released by molecular diffusion through the matrix of a solid polymer from the surface of the composition, the composition consisting essentially of kraft lignin a biodegradable solid solution of a water-insoluble polymer which is soluble in the pesticide in a diffusible component, including a pesticide which is non-reactive with the organic polymer, the diffusible component present in an amount equal to or greater than 50 percent by weight relative to the weight of the organic polymer so that when the outer surfaces of the composition are exposed to the environment, the diffusible component, including the pesticide, escapes from the composition, resulting in loss of structural integrity and disintegration of the outer surfaces only of the composition to expose new, undisintegrated surfaces of the composition containing a diffusible component for further release thereof over an extended period of time.

7. The solid, controlled release pesticide composition of claim 6 wherein the pesticide is Carbofuran.

8. A shaped, solid, controlled release pesticide composition for application in or on the soil wherein the pesticide is released to the soil by molecular diffusion through the matrix of the solid polymer at the surfaces of the composition exposed to the soil, the composition consisting essentially of:
an intimate mixture of kraft lignin and a component containing Carbofuran present in the composition in an amount such that when the outer surfaces of the shaped composition are exposed to the soil, the component present in the outer surfaces of the shaped composition diffuses into the soil, resulting in loss of the structural integrity and disintegration of the kraft lignin at those outer surfaces to expose new surfaces of the composition to the soil for further release of the component over an extended period of time until the component and kraft lignin are substantially dissipated.

9. A method of protecting plants from pests over an extended period of time, comprising:
applying to the soil in which the plant to be protected is located, an amount of a shaped composition effective to control the pest, the composition consisting essentially of an intimate mixture of kraft lignin and a component containing an organic, systemic pesticide, wherein the pesticide is released to the soil by molecular diffusion through the matrix of the kraft lignin polymer at the surfaces of the polymer exposed to the soil, the component present in the composition in an amount sufficient such that diffusion of the component into the soil at the surfaces of the composition exposed to the soil results in loss of the structural integrity and disintegration of the kraft lignin polymer at the exposed surfaces to thereby expose new surfaces of the composition to the soil for further diffusion of the component to the soil over an extended period of time until the component including the organic, systemic pesticide is substantially dissipated.

10. A shaped, controlled release pesticide composition for application in or on the soil wherein the pesticide is released to the soil by molecular diffusion through the matrix of kraft lignin at the surfaces of the composition exposed to the soil, the composition consisting of an intimate mixture of kraft lignin and Carbofuran, with the Carbofuran present in the composition in an amount at least 50 percent by weight, relative to the weight of the kraft lignin, the composition, when exposed to the soil, resulting in diffusion of the Carbofuran into the soil and disintegration of the kraft lignin at the outer surfaces of the composition exposed to the soil, with resulting exposure of new surfaces of the composition to the soil for sustained release of the Carbofuran over an extended period of time.

11. The composition of claim 1 wherein the diffusible component is a pesticide present in the composition in an amount equal to or greater than 50 percent by weight relative to the organic polymer so that the pesticide forms the matrix of the composition.

12. The composition of claim 1 wherein the diffusible component includes a pesticide and a water-soluble substance inert with respect to the pesticide, the component present in an amount equal to or greater than 50 percent by weight relative to the organic polymer and wherein the water-soluble substance diffuses simultaneously with the pesticide.

13. The composition of claim 1 wherein the diffusible component includes a substantially water-insoluble pesticide and a water-soluble material inert with respect to the pesticide, the diffusible component present in the composition in an amount equal to or greater than 50 percent by weight relative to the organic polymer and wherein the water-soluble material diffuses into the environment on exposure thereto, carrying the insoluble pesticide therewith.

14. The method of claim 5 wherein the pesticide is an organic, systemic pesticide.

15. The method of claim 9 wherein the pesticide is Carbofuran present in an amount greater than 50 percent by weight relative to the kraft lignin.

* * * * *

UNITED STATES PATENT AND TRADEMARK OFFICE
CERTIFICATE OF CORRECTION

PATENT NO. : 4,554,155

DATED : November 19, 1985

INVENTOR(S) : George G. Allan et al.

It is certified that error appears in the above—identified patent and that said Letters Patent is hereby corrected as shown below:

On the cover sheet, item 63, please change "Jan. 17, 1975" to --Jan. 17, 1974--.

Col. 13, line 59, "and a biodegradable" should be -- as a biodegradable --.

Signed and Sealed this

Twenty-eighth Day of April, 1987

*Attest:*

DONALD J. QUIGG

*Attesting Officer*    *Commissioner of Patents and Trademarks*